(12) United States Patent
Carter

(10) Patent No.: US 6,955,659 B1
(45) Date of Patent: Oct. 18, 2005

(54) STABILIZING ADHESIVE BODY FOR CATHETER

(76) Inventor: Dewey G. Carter, 853 Heather Rd., Suite A, Burlington, NC (US) 27215

( * ) Notice: Subject to any disclaimer, the term of this patent is extended or adjusted under 35 U.S.C. 154(b) by 0 days.

(21) Appl. No.: 10/431,410

(22) Filed: May 7, 2003

(51) Int. Cl.$^7$ ............................................. A61M 5/32
(52) U.S. Cl. .................................................. 604/180
(58) Field of Search ........................... 604/164.04, 174, 604/179, 180, 351, 385.03, 386, 387

(56) References Cited

U.S. PATENT DOCUMENTS

| | | | |
|---|---|---|---|
| 3,826,254 A | | 7/1974 | Mellor ........................ 128/133 |
| 3,834,380 A | * | 9/1974 | Boyd ........................... 604/180 |
| 3,885,560 A | * | 5/1975 | Baldwin ...................... 604/177 |
| 4,059,105 A | * | 11/1977 | Cutruzzula et al. .......... 604/180 |
| 4,324,236 A | * | 4/1982 | Gordon et al. ............... 604/272 |
| 4,324,237 A | * | 4/1982 | Buttaravoli ................... 602/54 |
| 4,460,356 A | | 7/1984 | Moseley ...................... 604/180 |
| 4,490,141 A | * | 12/1984 | Lacko et al. ................. 604/180 |
| 4,563,177 A | | 1/1986 | Kamen ........................ 604/177 |
| 4,698,057 A | | 10/1987 | Joishy ......................... 604/176 |
| 4,822,342 A | | 4/1989 | Brawner ...................... 604/180 |
| 4,838,868 A | * | 6/1989 | Forgar et al. ................ 604/180 |
| 5,087,248 A | * | 2/1992 | Beisang, III ................. 604/180 |
| 5,215,532 A | | 6/1993 | Atkinson ..................... 604/180 |
| 6,436,073 B1 | | 8/2002 | von Teichert ............... 604/174 |

* cited by examiner

*Primary Examiner*—Manuel Mendez
(74) *Attorney, Agent, or Firm*—MacCord Mason PLLC

(57) ABSTRACT

An infusion system for intravenous fluid injection. The apparatus includes: a catheter; and a stabilizing apparatus for the catheter. In the preferred embodiment, the stabilizing apparatus includes: (i) an anterior portion adhered to the catheter; (ii) an anterior folding portion adjacent to the anterior portion extending forwardly; (iii) a contact adhesive covering one surface of the stabilizing apparatus; (iv) a protective layer adhered to the contact adhesive; (v) a posterior portion; (vi) a posterior folding portion adjacent to the posterior portion extending rearward; (vii) a contact adhesive on a surface of the posterior portion; and (viii) a protective layer adhered to the contact adhesive on the posterior portion. The infusion system may also include a container for holding the intravenous fluid.

8 Claims, 3 Drawing Sheets

STABILIZING ADHESIVE BODY FOR CATHETER

BACKGROUND OF THE INVENTION (1) Field of the Invention

The present invention relates generally to infusion systems for intravenous fluid injection and, more particularly, to a stabilizing apparatus for an infusion system including a catheter for intravenous fluid injection.

(2) Description of the Prior Art

Infusion sets have been used in the medical world for many years to introduce and remove fluids from a patient's body. The set typically consists of a catheter or hollow needle mounted to a backing pad, a length of tubing connected at a first end to the catheter, and a connection fitting attached to a second end of the tubing. The catheter is inserted into a patient's vein and the backing pad is then secured to the patient's skin, usually with surgical tape. A supply of fluid to be infused into the patient is connected to the connection fitting and allowed to flow, by means of gravity, through the tubing, into the catheter and into the patient's vein.

If the catheter is not properly secured to the patient's skin, the catheter may be dislodged. Further, if the angle at which the catheter is inserted into the patient's vein is not maintained, it is possible for the catheter to puncture a lower wall of the vein, preventing effective introduction of the infusion fluid into the patient's vein. A means of anchoring the catheter securely in place is needed to avoid dislodging or movement of the catheter by the patient. Also, this system protects the patient from contamination of multiple use tape from patient to patient as well as eliminating aerosol and/or fluid contamination from the tape being stuck to nearby objects such as beds, desks, tables etc. before being applied to the patient.

SUMMARY OF THE INVENTION

The present invention is directed to an infusion system for intravenous fluid injection. The apparatus includes: a catheter; and a stabilizing apparatus for the catheter. In the preferred embodiment, the stabilizing apparatus includes: (i) an anterior portion adhered to the catheter; (ii) an anterior folding portion adjacent to the anterior portion extending forwardly; (iii) a contact adhesive covering one surface of the stabilizing apparatus; (iv) a protective layer adhered to the contact adhesive; (v) a posterior portion; (vi) a posterior folding portion adjacent to the posterior portion extending rearward; (vii) a contact adhesive on a surface of the posterior portion; and (viii) a protective layer adhered to the contact adhesive on the posterior portion. The infusion system may also include a container for holding the intravenous fluid.

In the preferred embodiment, the posterior folding portion is rotatable about an axis defined by a position where the posterior portion meets the posterior folding portion.

Also, in the preferred embodiment, the rearwardly extending length of the posterior folding portion is less than a distance between the position where the posterior portion meets the posterior folding portion and a position where the anterior portion meets the anterior folding portion. In the preferred embodiment, the posterior portion is attached to the catheter and, most preferably, is attached to the anterior portion.

Finally, the protective layer may include a tab for removing the protective layer.

Accordingly, one aspect of the present invention is to provide an infusion system for intravenous fluid injection, the apparatus comprising: a catheter; and a stabilizing apparatus for the catheter, the stabilizing apparatus including: (i) an anterior portion adhered to the catheter; (ii) an adjacent portion extending forwardly; (iii) a contact adhesive covering one surface of the stabilizing strip; and (iv) a protective layer adhered to the contact adhesive.

Another aspect of the present invention is to provide a stabilizing apparatus for an infusion system including a catheter for intravenous fluid injection, the stabilizing apparatus comprising: an anterior portion adhered to the catheter; an anterior folding portion adjacent to the anterior portion extending forwardly; a contact adhesive covering one surface of the stabilizing apparatus; and a protective layer adhered to the contact adhesive.

Still another aspect of the present invention is to provide an infusion system for intravenous fluid injection, the apparatus comprising: a catheter; and a stabilizing apparatus for the catheter, the stabilizing apparatus including: (i) an anterior portion adhered to the catheter; (ii) an anterior folding portion adjacent to the anterior portion extending forwardly; (iii) a contact adhesive covering one surface of the stabilizing apparatus; (iv) a protective layer adhered to the contact adhesive; (v) a posterior portion; (vi) a posterior folding portion adjacent to the posterior portion extending rearward; (vii) a contact adhesive on a surface of the posterior portion; and (viii) a protective layer adhered to the contact adhesive on the posterior portion; and a container for holding the intravenous fluid.

These and other aspects of the present invention will become apparent to those skilled in the art after a reading of the following description of the preferred embodiment when considered with the drawings.

DESCRIPTION OF THE PREFERRED EMBODIMENTS

Figure 1:
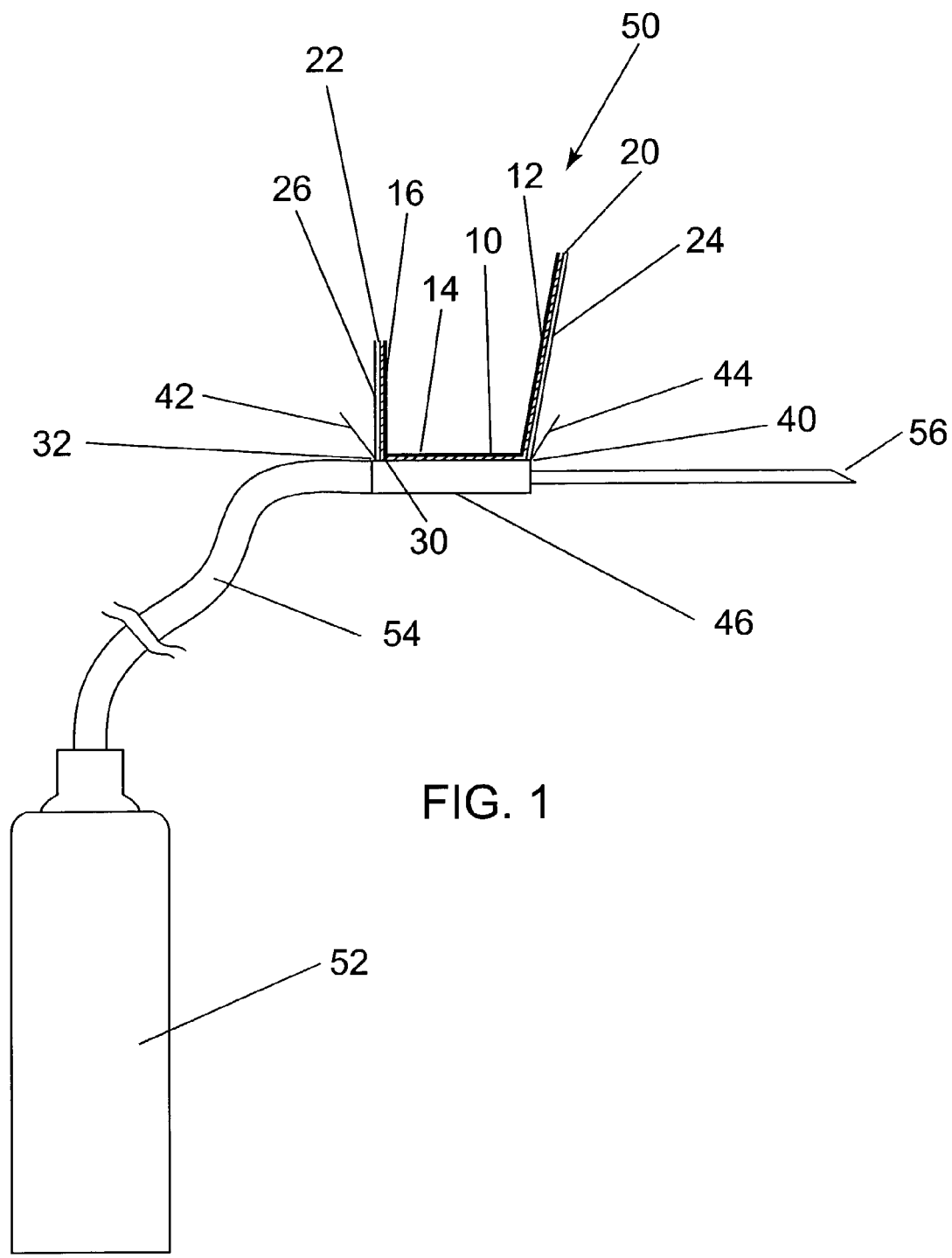
FIG. 1 is a side view of a stabilizing apparatus for an infusion system including a catheter for intravenous fluid injection constructed according to the present invention.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto. As best seen in FIG. 1, an infusion system for intravenous fluid injection is shown constructed according to the present invention. The infusion system for intravenous fluid injection may further include a butterfly catheter 46 connected by a tube 54 to a container 52 at an opening. The catheter may include a straight inline or circular catheter 62, (not shown in FIG. 1) or other types of catheters. The infusion system further includes a stabilizing apparatus 50 including an anterior portion 10 adhered to the catheter, an anterior folding portion 12 adjacent the anterior portion 10 and extending forwardly toward the insertion point of the catheter when the stabilizing apparatus 50 is used. The stabilizing apparatus 50 is covered on one surface by a contact adhesive 20 and further includes a protective layer 24 adhered to the contact adhesive 20. The protective layer 24 includes a tab 44 for removing the protective layer during use of the stabilizing apparatus 50.

The stabilizing apparatus 50 may further include a posterior portion 14 adhered to the catheter or, alternatively, to the anterior portion 10 as shown in FIG. 1. The stabilizing apparatus 50 may further include a posterior folding portion 16 adjacent to the posterior portion 14 and extending rearward when the stabilizing apparatus 50 is used. The stabilizing apparatus 50 may further include a contact adhesive 22 on a surface of the posterior portion 14, a protective layer 26 adhered to the contact adhesive 22, and a tab 42 for removing the protective layer 26.

Figure 2:
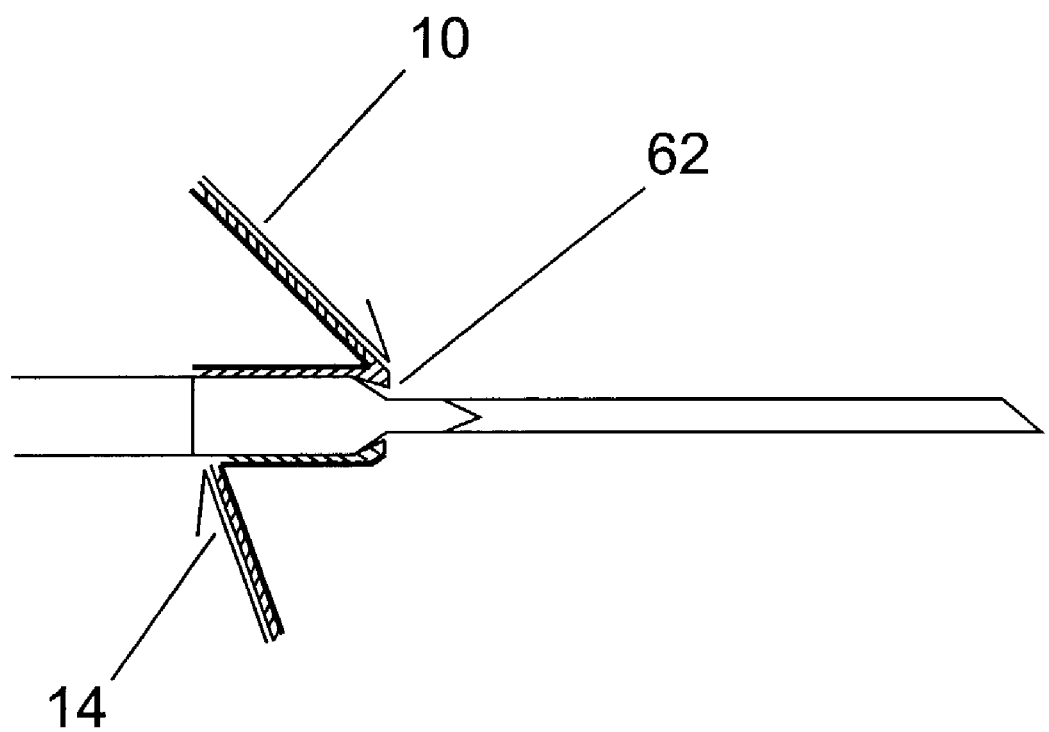
FIG. 2 is a side view of an alternative embodiment of the stabilizing apparatus for an infusion system including a circular catheter for intravenous fluid injection constructed according to the present invention.

FIG. 2 is a side view of the infusion system for intravenous fluid injection. The system is shown with a straight inline or circular catheter 62. In FIG. 2, the anterior portion 10 of the stabilizing apparatus is adhered to the top of the catheter 62 in use and the posterior portion 14 to the underside, both foldable to present a wing for grasping the stabilizing apparatus when inserting the catheter 62 into a patient.

Figure 3:
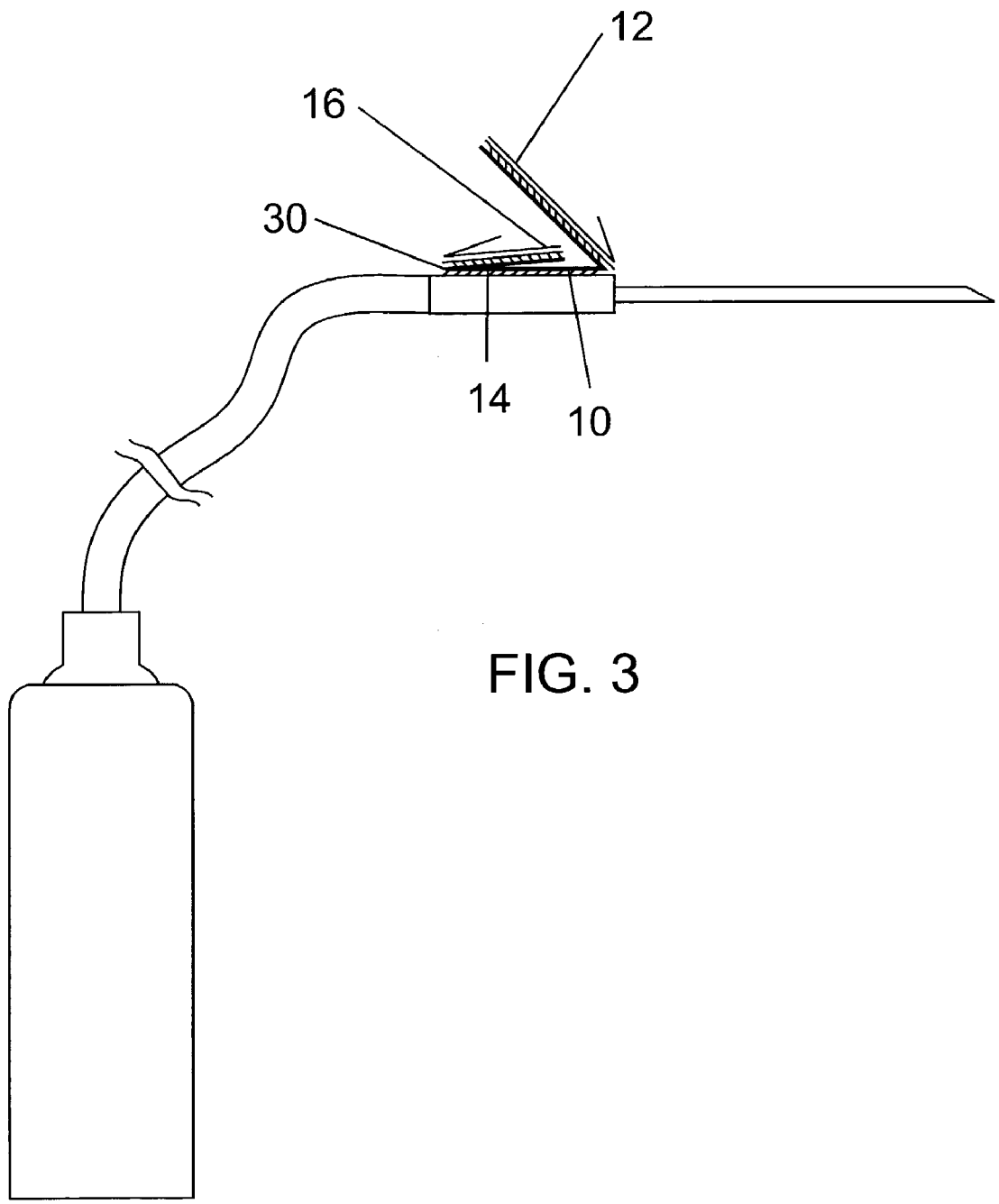
FIG. 3 is a side view of a stabilizing apparatus for an infusion system including a catheter for intravenous fluid injection constructed according to the present invention showing the stabilizing apparatus in a partially folded position.

FIG. 3 is a side view of an infusion system for intravenous fluid injection showing the stabilizing apparatus in a partially folded position. The posterior folding portion 16 may be rotatable about an axis 30 defined by an axis where the posterior portion 14 meets the posterior folding portion 16. In the preferred embodiment of the invention, the length of the posterior folding portion 14 is less than the distance 36 between such axis 30 and the position where the anterior folding portion 12 meets the anterior portion 10. This allows the posterior folding portion 16 to fold forward, rotating about the axis 30, before the anterior folding portion 12 folds rearward on top of the posterior folding portion 16. Such a position allows for convenient and cost-effective storage of the stabilizing system prior to use.

Certain modifications and improvements will occur to those skilled in the art upon a reading of the foregoing description. By way of example, the adhesive body configuration could extend laterally as well as being a part of the forward extending adhesive body. It should be understood that all such modifications and improvements have been deleted herein for the sake of conciseness and readability but are properly within the scope of the following claims.

What is claimed is:

1. A stabilizing apparatus for an infusion system including a catheter for intravenous fluid injection, said stabilizing apparatus comprising:
   (a) an anterior portion adhered to said catheter;
   (b) an anterior folding portion adjacent to said anterior portion extending forwardly;
   (c) a contact adhesive covering one surface of said stabilizing apparatus; and
   (d) a protective layer adhered to said contact adhesive.

2. A stabilizing apparatus according to claim 1 further including: (i) a posterior portion; (ii) a posterior folding portion adjacent to said posterior portion extending rearward; (iii) a contact adhesive on a surface of said posterior portion; and (iv) a protective layer adhered to said contact adhesive on said posterior portion.

3. A stabilizing apparatus according to claim 2 wherein said posterior folding portion is rotatable about an axis defined by a position where the posterior portion meets said posterior folding portion.

4. A stabilizing apparatus according to claim 3 wherein the rearwardly extending length of said posterior folding portion is less than a distance between said position where the posterior portion meets said posterior folding portion and a position where said anterior portion meets said anterior folding portion.

5. A stabilizing apparatus according to claim 2 wherein said protective layer includes a tab for removing said protective layer.

6. A stabilizing apparatus according to claim 2 wherein said posterior portion is attached to said catheter.

7. A stabilizing apparatus according to claim 2 wherein said posterior portion is attached to said anterior portion.

8. A stabilizing apparatus according to claim 1 wherein said protective layer includes a tab for removing said protective layer.

* * * * *